(12) United States Patent
Sauerer et al.

(10) Patent No.: US 11,029,250 B2
(45) Date of Patent: Jun. 8, 2021

(54) WELLSITE KEROGEN MATURITY DETERMINATION UTILIZING RAMAN SPECTROSCOPY

(71) Applicant: SCHLUMBERGER TECHNOLOGY CORPORATION, Sugar Land, TX (US)

(72) Inventors: Bastian Sauerer, Dhahran (SA); Wael Abdallah, Dhahran (SA)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 16/489,188

(22) PCT Filed: Feb. 21, 2018

(86) PCT No.: PCT/US2018/018869
§ 371 (c)(1),
(2) Date: Aug. 27, 2019

(87) PCT Pub. No.: WO2018/156527
PCT Pub. Date: Aug. 30, 2018

(65) Prior Publication Data
US 2020/0003694 A1 Jan. 2, 2020

Related U.S. Application Data

(60) Provisional application No. 62/464,158, filed on Feb. 27, 2017.

(51) Int. Cl.
*G01J 3/44* (2006.01)
*G01N 21/65* (2006.01)
*G01N 33/28* (2006.01)

(52) U.S. Cl.
CPC ............... *G01N 21/65* (2013.01); *G01J 3/44* (2013.01); *G01N 33/2823* (2013.01)

(58) Field of Classification Search
CPC .... G01N 21/65; G01N 21/64; G01N 33/2823; A61B 5/0075; G01J 3/44
See application file for complete search history.

(56) References Cited

U.S. PATENT DOCUMENTS

2003/0163259 A1    8/2003  DiFoggio et al.
2007/0081157 A1*   4/2007  Csutak ................... G01N 21/39
                                                    356/301

(Continued)

OTHER PUBLICATIONS

C. F. K. Diessel, R. N. Brothers, P. M. Black. "Coalification and graphitization in high-pressure schists in New Caledonia." Contributions to Mineralogy and Petrology 1978, 68, 63-78.

(Continued)

*Primary Examiner* — Abdullahi Nur
(74) *Attorney, Agent, or Firm* — Trevor G. Grove

(57) ABSTRACT

A method for determining thermal maturity of a formation sample. The method includes: cleaning the formation sample to remove residues of drilling fluid and reservoir fluid to obtain a cleaned sample; performing Raman spectroscopic measurements on the cleaned sample to obtain a Raman spectrum for the cleaned sample; fitting at least a G (graphite) peak and a D1 (defect) peak to the Raman spectrum to obtain Raman shift values for the G peak and the D1 peak and a Raman band separation (RBS) value; using the RBS to generate a vitrinite reflection equivalent ($V_{Re}$) value using a relationship correlating RBS to $V_{Re}$; and displaying the $V_{Re}$ as an indicator of formation sample maturity for a depth in the formation from which the cleaned sample was obtained.

20 Claims, 8 Drawing Sheets

(56) References Cited

U.S. PATENT DOCUMENTS

| | | |
|---|---|---|
| 2012/0234360 A1 | 9/2012 | Snape et al. |
| 2015/0090443 A1 | 4/2015 | Bryndzia et al. |
| 2015/0240633 A1 | 8/2015 | Akkurt et al. |

OTHER PUBLICATIONS

O. Beyssac, B. Goffé, C. Chopin, J. N. Rouzaud, "Raman spectra of carbonaceous material in metasediments: a new geothermometer." Journal of Metamorphic Geology 2002, 20, 859-871.
B. J. Cardott, M. A. Kidwai, "Graptolite reflectance as a potential thermal-maturation indicator." in K. S. Johnson, ed., "Late Cambrian-Ordovician Geology of the Southern Midcontinent, 1989 Symposium." Oklahoma Geological Survey Circular 1991, 92, 203-209.
H. I. Petersen, H. N. Schovsbo, A. T. Nielsen, "Reflectance measurements of zooclasts and solid bitumen in Lower Paleozoic shales, southern Scandinavia: Correlation to vitrinite reflectance." International Journal of Coal Geology 2013, 114, 1-18.
F. Goodarzi, "Reflected light microscopy of chitinozoan fragments" Marine and Petroleum Geology 1985, 2, 72-78.
F. Goodarzi, "Dispersion of optical properties of graphtolites with increased maturity in early Paleozoic organic rich sediments." Fuel 1985, 64, 1735-1740.
G. A. Cole, "Graptolite-chitinozoan reflectance and its relationship to other geochemical maturity indicators in the Silurian Qusaiba Shale, Saudi Arabia." Energy Fuels 1994, 8, 1443-1459.
K. E. Peters, "Guidelines for evaluating petroleum source rocks using programmed pyrolysis." Am. Assoc. Pet. Geol. Bull. 1986, 70, 318-329.
E. Lafargue, F. Marquis, D. Pillot, "Rock-eval 6 applications in hydrocarbon exploration, production, and soil contamination studies." Revue de L'institut Francais du Petrole 1998, 53, 421-437.
F. Behar, V. Beaumont, H. D. L Penteako, "Rock-eval 6 technology: performances and developments." Revue de L'institut Francais du Petrole 2001, 56, 111-134.
D. M. Jarvie, B. Claxton, B. Henk, J. Breyer, "Oil and Shale Gas from Barnett Shale, Ft. Worth Basin, Texas." AAPG National Convention 2001, Jun. 3-6, Denver, CO, USA.
C. A. Landis, "Graphitization of dispersed carbonaceous material in metamorphic rocks." Contributions to Mineralogy and Petrology 1971, 30, 34-45.
E. S. Grew, "Carbonaceous material in some metamorphic rocks of New England and other areas." Journal of Geology 1974, 82, 50-73.
Y. Nishimura, D. S. Coombs, C. A. Landis, T. Itaya, "Continuous metamorphic gradient documented by graphitization and K-Ar age, southeast Otago, New Zealand." American Mineralogist, 2000, 84, 1625-1636.
M. Bonijoly, M. Oberlin, A. Oberlin, "A possible mechanism for natural graphite formation." International Journal of Coal Geology 1982, 1, 283-312.
P. R. Buseck, B.-J. Huang, "Conversion of carbonaceous material to graphite during metamorphism." Geochimica et Cosmochimica Acta 1985, 49, 2003-2016.
O. Beyssac, J. N. Rouzaud, B. Goffé, F. Brunet, C. Chopin, "Characterization of high-pressure, low-temperature graphitization: a Raman microspectroscopy and HRTEM study" Contributions to Mineralogy and Petrology, 2002, 143, 19-31.
B. Wopenka, J. D. Pasteris, "Structural characterization of kerogens to granulite-facies graphite: applicability of Raman microprobe spectroscopy." American Mineralogist 1993, 78, 533-557.
F. Tuinstra, J. L. Koenig, "Raman Spectrum of Graphite." The Journal of Chemical Physics 1970, 53, 1126-1130.
C. P. Marshall, H. G. M. Edwards, J. Jehlicka, "Understanding the application of Raman spectroscopy to the detection of traces of life." Astrobiology 2010, 10, 229-243.
S. R. Kelemen, H. L. Fang, "Maturity trends in Raman spectra from kerogen and coal." Energy Fuels 2001, 15, 553-658.
A. Schmidt Mumm, S. Inan, "Microscale organic maturity determination of graptolites using Raman spectroscopy" International Journal of Coal Geology 2016, 162, 96-107.
J. D. Pasteris, B. Wopenka, "Raman spectra of graphite as indicators of degree of metamorphism." Canadian Mineralogist 1991, 29, 1-9.
T. F. Yui, E. Huang, J. Xu, "Raman spectrum of carbonaceous material: a possible metamorphic grade indicator for low-grade metamorphic rocks." Journal of Metamorphic Geology 1996, 14, 115-124.
C. Spötl, D. W. Houseknecht, R. C. Jaques, "Kerogen maturation and incipient graphitization of hydrocarbon source rocks in the Arkoma Basin, Oklahoma and Arkansas: a combined petrographic and Raman spectrometric study." Org. Geochem. 1998, 28, 535-542.
D. Liu, X. Xiao, H. Tian, Y. Min, Q. Zhou, P. Cheng, J. Shen, "Sample maturation calculated using Raman spectroscopic parameters for solid organics: methodology and geological applications." Chin. Sci. Bull. 2013, 58, 1285-1298.
Wilkins et al., 'Thermal maturity evaluation from inertinites by Raman spectroscopy: The 'RaMM' technique', International Journal of Coal Geology, 128-129 (2014), pp. 143-152.
Hackley et al., "Standardization of Reflectance Measurements in Dispersed Organic Matter; Results of an Exercise to Improve Interlaboratory Agreement", Marine and Petroleum Geology, vol. 59, pp. 22-34, 2015.

* cited by examiner

WELLSITE KEROGEN MATURITY DETERMINATION UTILIZING RAMAN SPECTROSCOPY

PRIORITY

This application claims priority from provisional U.S. patent application 62/464,158 filed on Feb. 27, 2017.

BACKGROUND

The present application relates to analysis of hydrocarbon-bearing formations. More particularly, the present application relates to analysis of the maturity of kerogen contained in a formation. Knowledge of the maturity of kerogen (e.g. in organic-rich mudstones such as shales or in tight carbonates) plays an important role in reservoir characterization of unconventional plays, as it provides information of the hydrocarbon type that is to be expected in the reservoir.

Kerogen thermal maturity can be determined by vitrinite reflectance measurements on the respective macerals in kerogen. See, Diessel, C. F. K. et al., "Coalification and Graphitization in High-Pressure Schists in New Caledonia", *Contributions to Mineralogy and Petrology*, 68, pp. 63-78 (1978). However, significant expertise is required for this method, which is also very labor intensive. In addition, in formations where vitrinite is not present, such as in formations deposited earlier than the Devonian period which lack the respective marcerals, no such determination can be made. In such cases, other methods have been developed to utilize the reflectance of other marcerals like graptolites or chitinozoans. See, e.g., Petersen, H. I., et al., "Reflectance Measurements of Zooclasts and Solid Bitumen in Lower Paleozoic Shales, Southern Scandinavia: Correlation to Vitrinite Reflectance," *International Journal of Coal Geology* 113, pp. 1-18 (2013). However, correlation of these methods to the vitrinite standard introduce another source of error, as there is an anisotropy in their reflectance pattern.

Another established method to estimate thermal maturity is the so-called Rock-Eval pyrolysis, where formation samples are subject to programmed heating and the amount of hydrocarbons generated from decomposition of kerogen is measured. See, e.g., Jarvie, D. M. et al., "Oil and shale Gas from Barnett Shale Ft. Worth Basin, Tex.," *AAPG National Convention*, June 3-6, Denver, Colo., (2001). Formations that have only low amounts of organic material or those who are highly mature do not show accurate estimates using this approach. Other methods, such as X-ray diffraction and high-resolution transmission electron microscopy are commonly used to study graphitization of organic matter. However, these methods work better in the high maturity region, which is not of interest for studying kerogen in the oil and gas windows.

Because of the shortcomings of the various methods in the art, most common maturity estimations are based on complex laboratory methods, which require the kerogen to be isolated from the rock matrix or the sample to be crushed. These methods are therefore destructive and time intensive.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In an embodiment, a formation maturity determination is made at a wellsite by obtaining drill cuttings at the wellsite, cleaning the drill cuttings at the wellsite, conducting Raman spectroscopic measurements on the cleaned cuttings at the wellsite, and utilizing a function of the Raman spectroscopic measurements in making a formation maturity determination. The formation maturity determinations may be presented in log format at the wellsite as a log of formation maturity as a function of drilling depth (distance).

In one embodiment, the Raman spectroscopic function used in making a formation maturity determination is the separation (RBS) between the determined D1 and G bands of the Raman spectrum resulting from the spectroscopic measurements. In one embodiment, the RBS is used to make the formation maturity determination by turning the RBS into a vitrinite reflectance equivalent via a correlation, and then using the vitrinite reflectance equivalent as a maturity indicator of the formation from which the cuttings were taken.

Other aspects and advantages will be apparent from the following description and the appended claims.

BRIEF DESCRIPTION OF DRAWINGS

The subject disclosure is further described in the detailed description which follows, in reference to the noted plurality of drawings by way of non-limiting examples of the subject disclosure, in which like reference numerals represent similar parts throughout the several views of the drawings, and wherein.

DETAILED DESCRIPTION

The particulars shown herein are by way of example and for purposes of illustrative discussion of the examples of the subject disclosure only and are presented in the cause of providing what is believed to be the most useful and readily understood description of the principles and conceptual aspects of the subject disclosure. In this regard, no attempt is made to show structural details in more detail than is necessary, the description taken with the drawings making apparent to those skilled in the art how the several forms of the subject disclosure may be embodied in practice. Furthermore, like reference numbers and designations in the various drawings indicate like elements.

Figure 1:
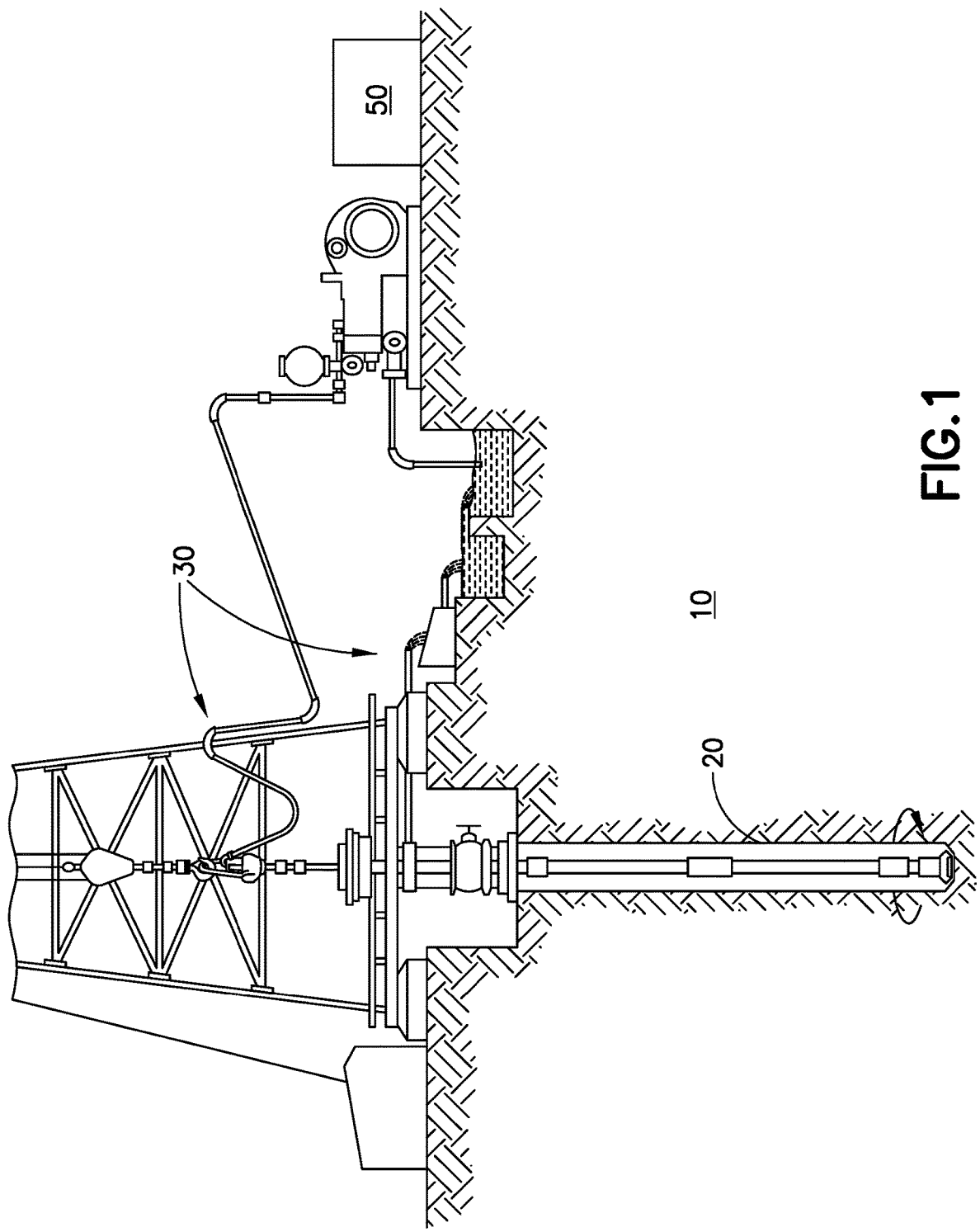
FIG. 1 is a diagram of a wellsite with equipment provided for generating a log of formation maturity as a function of drilling depth.

A formation 10 in which a well 20 is being drilled is seen in FIG. 1. Equipment 30 for drilling the formation is located on the surface of the formation and extends into the well 20 and typically includes a turn table, a kelly, drill pipe, a drill collar, a drill bit, a mud pump, shale shaker, etc. Also located on the surface of the formation is equipment 50 which permits the making of maturity determinations on formation rock which is being drilled.

Figure 1A:
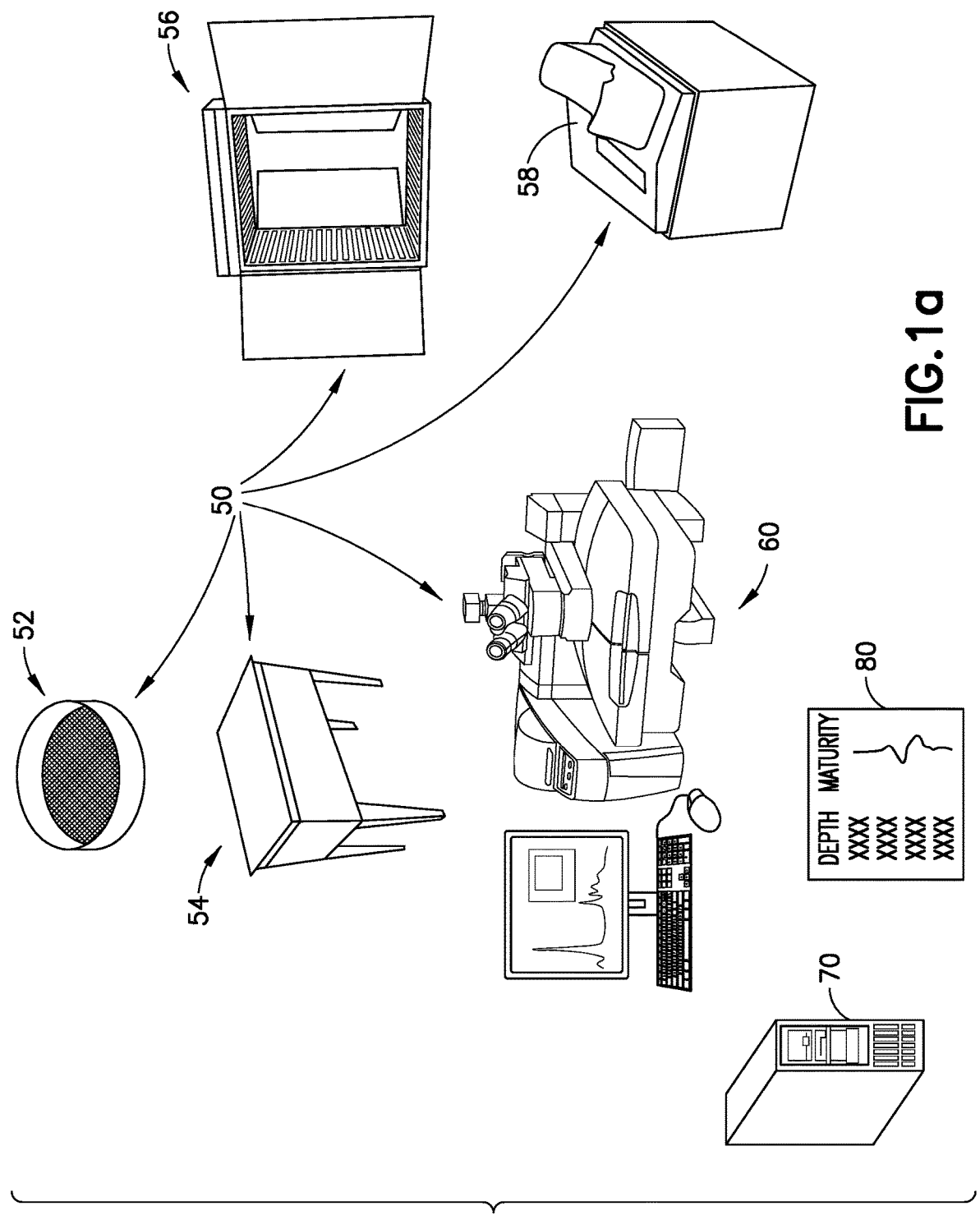
FIG. 1A is a block diagram of wellsite equipment used for obtaining, cleaning, drying, and analyzing sample cuttings from the formation from which a formation maturity log is generated.

Details of one embodiment of the equipment 50 are seen in FIG. 1A. Equipment 50 includes one or more sieves 52 that separate drill cuttings from drilling mud, a washing station 54 for cleaning the cuttings, a drying station 56 for drying the cleaned cuttings, an observation station 58 for checking to see whether the dry cuttings show signs of fluorescence, and a Raman spectrometer 60 for investigating the dry, clean cuttings. A computer or processor 70 may also be located at the wellsite (or remotely) for receiving information from the spectrometer and processing the information in order to generate an indication of the maturity of the formation from which the cuttings were obtained. The processed information is then presented as a log 80 which plots an indication of formation maturity as a function of wellbore depth. The log may be generated at the wellsite and/or remotely and may be presented as part of a multi-log which presents additional information regarding the formation and/or drilling process.

Figure 2:
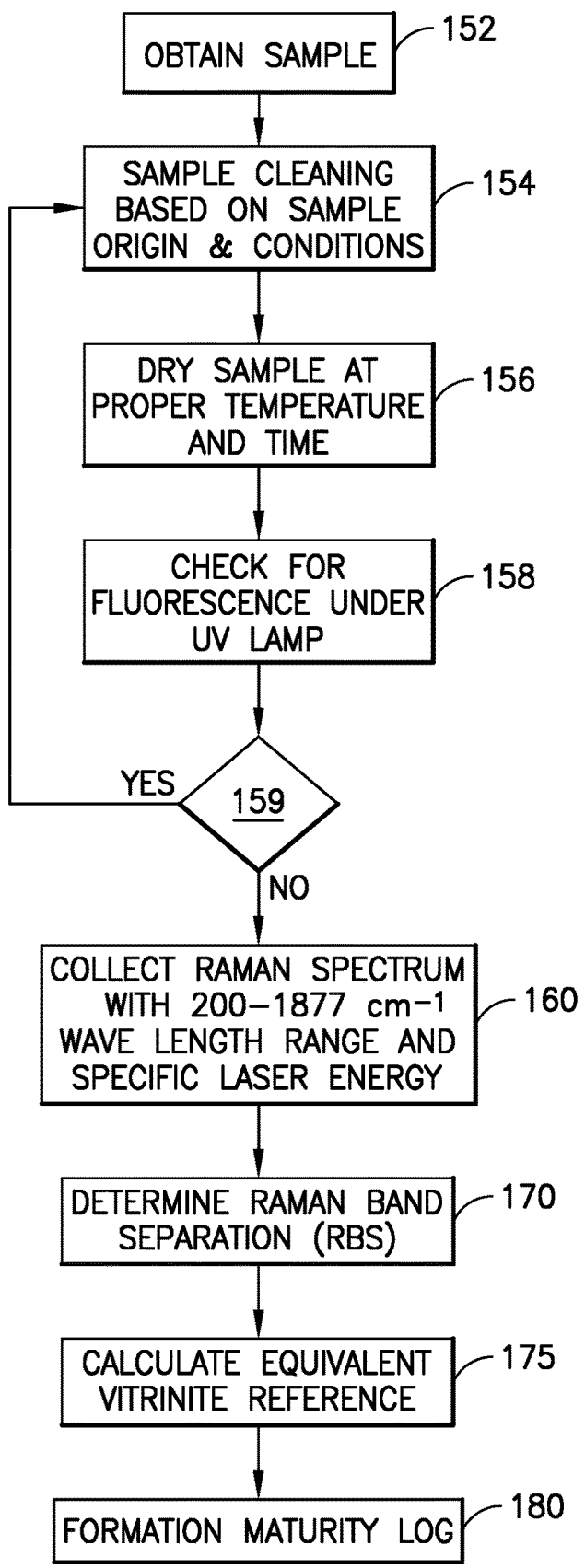
FIG. 2 is a flow diagram of a method for making maturity determinations on reservoir rocks.

Turning to FIG. 2, the equipment of FIG. 1A may be used as follows. Drill cuttings are collected at 152 at the wellsite (shale shaker), e.g., using sieves 52 and are identified as having come from a particular depth in the formation based on when they are received at the formation surface. The sieves may be of desired fineness so to receive cuttings of a desired size, e.g., greater than 2 mm. At 154, the cuttings are provided to the washing station 54, and depending on the drilling fluid used for drilling the wellbore, one of two cleaning procedures is executed to remove the reservoir and drilling fluids from the cuttings. If the well is drilled with oil based mud (OBM), in one embodiment, the cuttings are washed at washing station 54 with base oil, then with water, then with a mixture of water and soap, then again with pure water. In one embodiment, the base oil of the cleaning procedure may be diesel. If, on the other hand, the well is drilled with water based mud, in one embodiment, the cuttings are washed at washing station 54 with water. In an embodiment, an additional cleaning step utilizing an organic solvent is added. The organic solvent is selected based on solubility tests with non-kerogen hydrocarbon residues in the formation samples. In any event, the cleaning procedure is designed in a way to effectively remove residues of the respective drilling fluid (OBM or WBM) and any reservoir fluid from the rock samples.

In one embodiment, the cleaning procedure may be extended to utilize a surfactant. The surfactant may be selected based on cleaning tests with non-kerogen hydrocarbon residues in the formation samples.

After the cuttings are washed, at 156 they are transferred to the drying station 56. In one embodiment, the drying station 56 includes an oven set at 70° C. in which the washed cuttings are placed for a period of time e.g., fifteen minutes, to dry. After being removed from the oven, the now-dry cuttings are transferred to the observation station 58 where they are observed at 158 under a UV lamp. If, at 159, the cuttings show any signs of fluorescence, the cleaning procedure for OBM drilled samples (e.g., using base oil, then water, then water and soap, and then pure water) is repeated at 154 on the samples, irrespective of the drilling fluid that was used. If the cleaning is repeated, after the cleaning process, the cuttings are again sent back to the drying station 56 for drying and to the observation station 58 for UV checking. Samples that do not show fluorescence after the drying step are provided at 160 for analysis on the sample stage of the Raman spectrometer 60. The Raman measurement is executed on the cleaned, dried rock samples and requires no further sample preparation.

At 160, acquisition parameters are set and the Raman microscope objective is focused on the sample surface. The spectrum is acquired and processed at 170 using processor 70 by fitting G, D1, D2, D3, and D4 peaks as is discussed below with reference to FIGS. 3A and 3B. The G (graphite) peak indicates well-ordered, graphite-like carbon structures in the kerogen and is due to the in-plane $E_{2g2}$ vibrational modes of the $sp^2$ carbon atoms in aromatic ring structures exhibiting $D_{6h}^4$ symmetry. The D1 (defect) peak results from Raman-active $A_{1g}$ symmetry and is connected to lattice defects and discontinuities of the $sp^2$ carbon network. D2, D3 and D4 are further defect peaks identified in Raman spectra of carbonaceous material. At 170, using the processor 70, the positions ωG and ωD1 of the G and D1 peak respectively are extracted and the Raman band separation RBS=ωG−ωD1 is calculated. A correlation as discussed hereinafter with reference to FIG. 4, created from organic-rich mudstones with known vitrinite reflectance, may then be used at 175 to convert the RBS value obtained from the Raman spectroscopic measurement on the cutting to a vitrinite reflectance equivalent value ($V_{Re}$) which represents the maturity of the respective formation interval from which the cutting was obtained. See, Hackley, Paul C., et al., "Standardization of Reflectance Measurements in Dispersed Organic Matter; Results of an Exercise to Improve Interlaboratory Agreement, *Marine and Petroleum Geology* 59 pp. 22-34 (2015). When cuttings from different depths in the formation are processed according to steps 152-175, the $V_{Re}$ values may then be plotted as a log at 180 and as discussed hereinafter with respect to FIG. 5.

In one embodiment, the Raman spectrometer comprises a Raman microscope such as the Thermo Scientific DXR Raman Microscope sold by Thermo Fisher Scientific, Inc. of Waltham, Mass. In one embodiment, the Raman spectrometer utilizes a Raman laser having a wavelength of approximately 532 nm; i.e., 532 nm±5 nm. In other embodiments, the wavelength of the Raman laser is any wavelength that produces a better signal to noise ratio than the wavelength of approximately 532 nm.

Figure 3A:
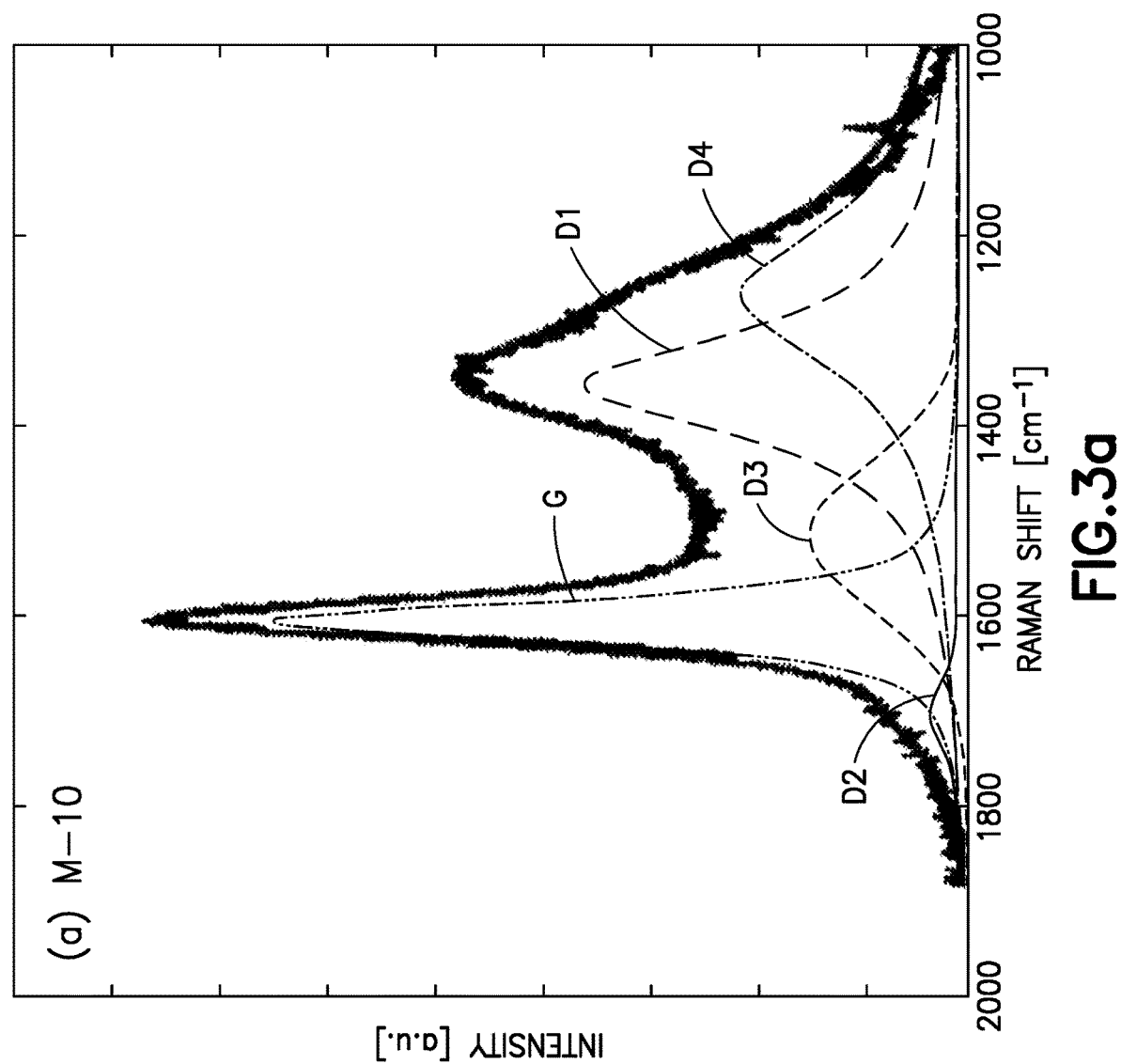
FIGS. 3A-3C are respectively exemplary spectral deconvolution plots showing intensity versus Raman shift for two samples, and a measured Raman spectra plot for eleven samples stacked in order of increasing thermal maturity and offset for clarity.
Figure 3B:
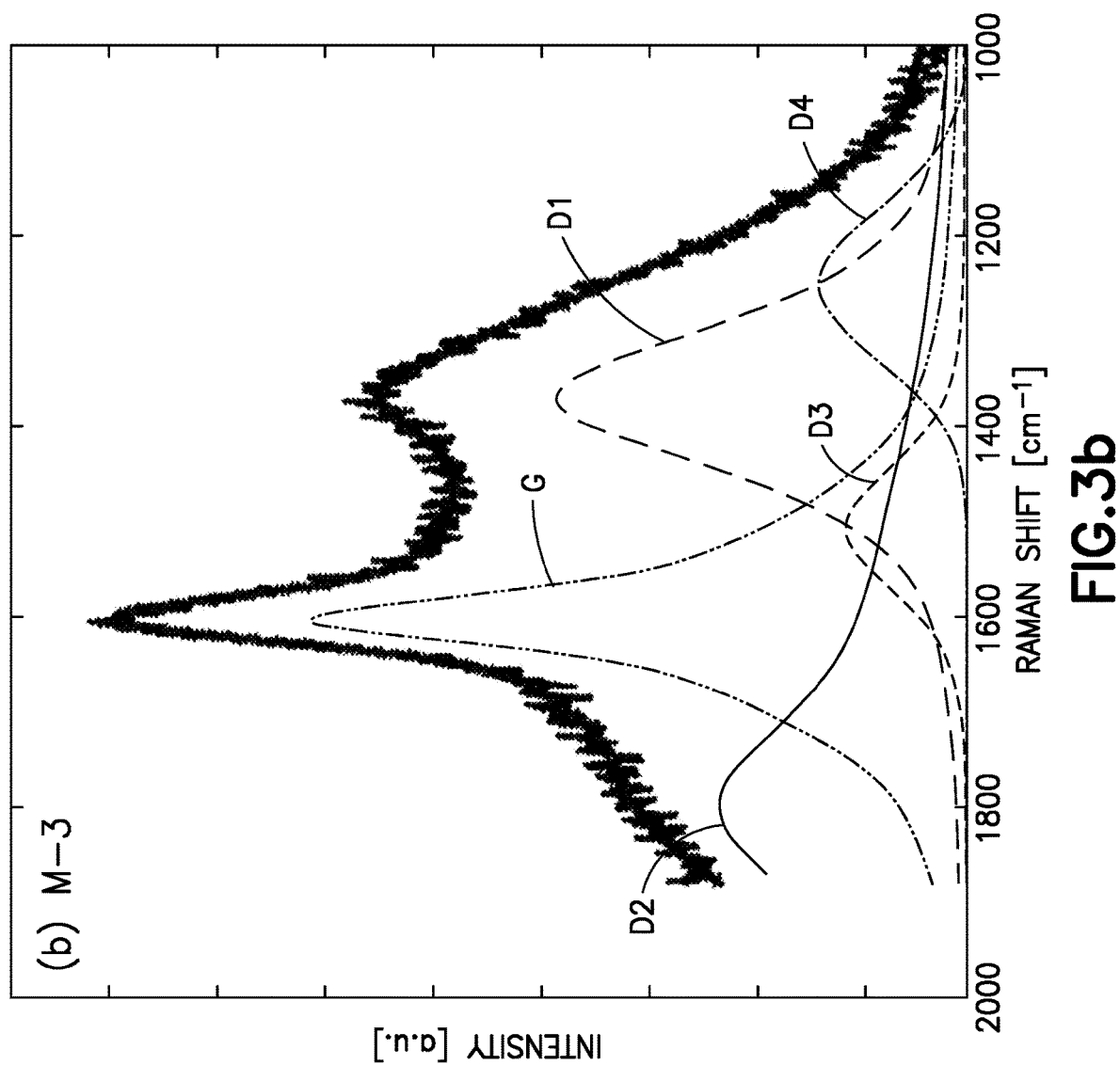

In building the RBS—vitrinite correlation, Raman spectra were acquired using a Thermo Scientific DXR Raman microscope. Monochromatic excitation was performed with a 532 nm laser, which was focused on the sample with a ten-times magnification objective resulting in an estimated spot size of 2.1 μm. Laser wavelength calibration, white light calibration, and laser frequency calibration were performed before measuring the samples. Laser power was set to 10 mW. A twenty-five μm slit was used as an aperture. The grating was set to 1800 lines/mm. Spectra were acquired from 1877 to 200 cm$^{-1}$. The Raman spectra were acquired and processed using OMNIC v.9.3.03 software of Thermo Scientific. Automated fluorescence correction was applied. For each of eleven samples with known vitrinite reflectance, twenty-five Raman spectra were collected at different locations on the sample surface, representing different topological features. Each spectrum was an average of sixteen scans. Acquisition of each spectrum was obtained in less than two minutes. Deconvolution and fitting of the Raman spectra were made using five peaks with mixed Guassian/Lorentzian profiles and a linear baseline correction. Spectral and peak fitting results for two of the samples are shown in FIGS. 3A and 3B. No constraints were put on the peak parameters in the curve fitting procedure in order to allow for an optimal fit to the measured spectra. The band positions, amplitudes (intensities), full-widths at half maximum, and integrated areas of all peaks were extracted from the resulting curve fits. It was found that although the twenty-five spectra for each sample showed significant ranges in the peak widths, intensities, and areas, as shown below in Table 1, the mean G and D1 band positions and the mean RBS for any particular sample could be reliably extracted from the spectra with an average deviation of ±2.7 cm$^{-1}$.

In one embodiment, the RBS and vitrinite reflectance are related according to the relationship RBS=c1 ln(x)+c2, where c1 and c2 are constants, and x is the vitrinite reflectance. Example values for c1 and c2 are 18.595 and 236.78, although other values may be found depending upon the Raman spectral equipment being utilized and the settings for that equipment that are utilized.

According to one aspect, since a correlation exists between the RBS of a sample and the vitrinite reflectance, when a cutting is retrieved from wellbore, cleaned as previously described to remove any contaminants, and then subjected to a Raman spectroscopic measurement, the RBS

TABLE 1

Geochemical characteristics of kerogen in organic-rich mudstones

| | | | Vitrinite reflectance[a] Rock-Eval[b] | | | Raman | | |
|---|---|---|---|---|---|---|---|---|
| | | | S2 [mg | | | | | |
| Sample ID | TOC [wt %] | % Ro mean | N | HC/g rock] | $T_{max}$ [° C.] | $T_{max}$maturity [% VRe] | G position $W_G$ [cm$^{-1}$] | D1 position $W_{D1}$ [cm$^{-1}$] | RBS, $W_G - W_{D1}$ [cm$^{-1}$] |
| M-1 | 15.7 | 0.55 | — | 129.5 | 416 | 0.3 | 1585.1 ± 3.2 | 1377.0 ± 4.1 | 208.0 ± 4.5 |
| M-2 | 4.8 | 2.2 | — | 0.2 | — | — | 1604.3 ± 1.1 | 1349.5 ± 1.1 | 254.8 ± 0.9 |
| M-3 | 4.4 | 0.75 | 25 | 9.6 | 442 | 0.8 | 1599.7 ± 1.2 | 1367.0 ± 4.8 | 229.7 ± 5.4 |
| M-4 | 5.0 | 0.8 | 14 | 10.8 | 441 | 0.8 | 1598.7 ± 1.7 | 1367.0 ± 5.1 | 231.7 ± 5.3 |
| M-5 | 5.8 | 0.55 | 41 | 22.7 | 434 | 0.7 | 1597.7 ± 1.8 | 1373.5 ± 4.3 | 224.2 ± 3.7 |
| M-6 | 5.9 | 0.7 | 40 | 18.0 | 435 | 0.7 | 1597.9 ± 1.3 | 1369.3 ± 3.7 | 228.6 ± 3.9 |
| M-7 | 4.1 | 0.9 | 52 | 3.4 | 446 | 0.9 | 1600.9 ± 0.6 | 1361.3 ± 2.7 | 239.6 ± 2.9 |
| M-8 | 4.3 | 1.55 | 40 | 0.6 | — | — | 1601.9 ± 1.2 | 1360.7 ± 3.8 | 241.2 ± 3.5 |
| M-9 | — | 4.3 | 80 | 0.1 | — | — | 1601.9 ± 2.1 | 1340.2 ± 2.9 | 261.7 ± 2.8 |
| M-10 | 11.0 | 1.4 | 17 | 4.0 | 470 | 1.3 | 1602.7 ± 1.1 | 1359.6 ± 2.2 | 243.1 ± 2.0 |
| M-11 | 7.6 | 1.4 | — | 2.6 | 474 | 1.4 | 1601.0 ± 1.4 | 1355.4 ± 1.2 | 245.6 ± 1.4 |

| | Raman | | |
|---|---|---|---|
| Sample ID | (D1/G)$_{Area}$ | (D1/G)$_{Intensity}$ | (D1/[D1 + D2 + G])$_{Area}$ |
| M-1 | 0.25 ± 0.12 | 0.45 ± 0.07 | 0.29 ± 0.10 |
| M-2 | 1.87 ± 0.23 | 0.56 ± 0.03 | 0.26 ± 0.09 |
| M-3 | 0.70 ± 0.25 | 0.63 ± 0.04 | 0.36 ± 0.09 |
| M-4 | 0.61 ± 0.14 | 0.60 ± 0.04 | 0.34 ± 0.08 |
| M-5 | 0.57 ± 0.12 | 0.63 ± 0.04 | 0.27 ± 0.06 |
| M-6 | 0.66 ± 0.28 | 0.58 ± 0.07 | 0.53 ± 0.05 |
| M-7 | 1.00 ± 0.35 | 0.54 ± 0.07 | 0.62 ± 0.09 |
| M-8 | 0.95 ± 0.28 | 0.53 ± 0.11 | 0.30 ± 0.07 |
| M-9 | 2.72 ± 1.07 | 0.94 ± 0.13 | 0.45 ± 0.04 |
| M-10 | 0.81 ± 0.25 | 0.47 ± 0.06 | 0.14 ± 0.05 |
| M-11 | 1.41 ± 0.29 | 0.50 ± 0.06 | 0.28 ± 0.08 |

[a]vitrinite maceral count (N) reported where provided as histograms by the laboratory
[b]vitrinite reflectance equivalent from $T_{max}$: % $V_{re}$ = [0.018 * $T_{max}$] − 7.16

Figure 3C:
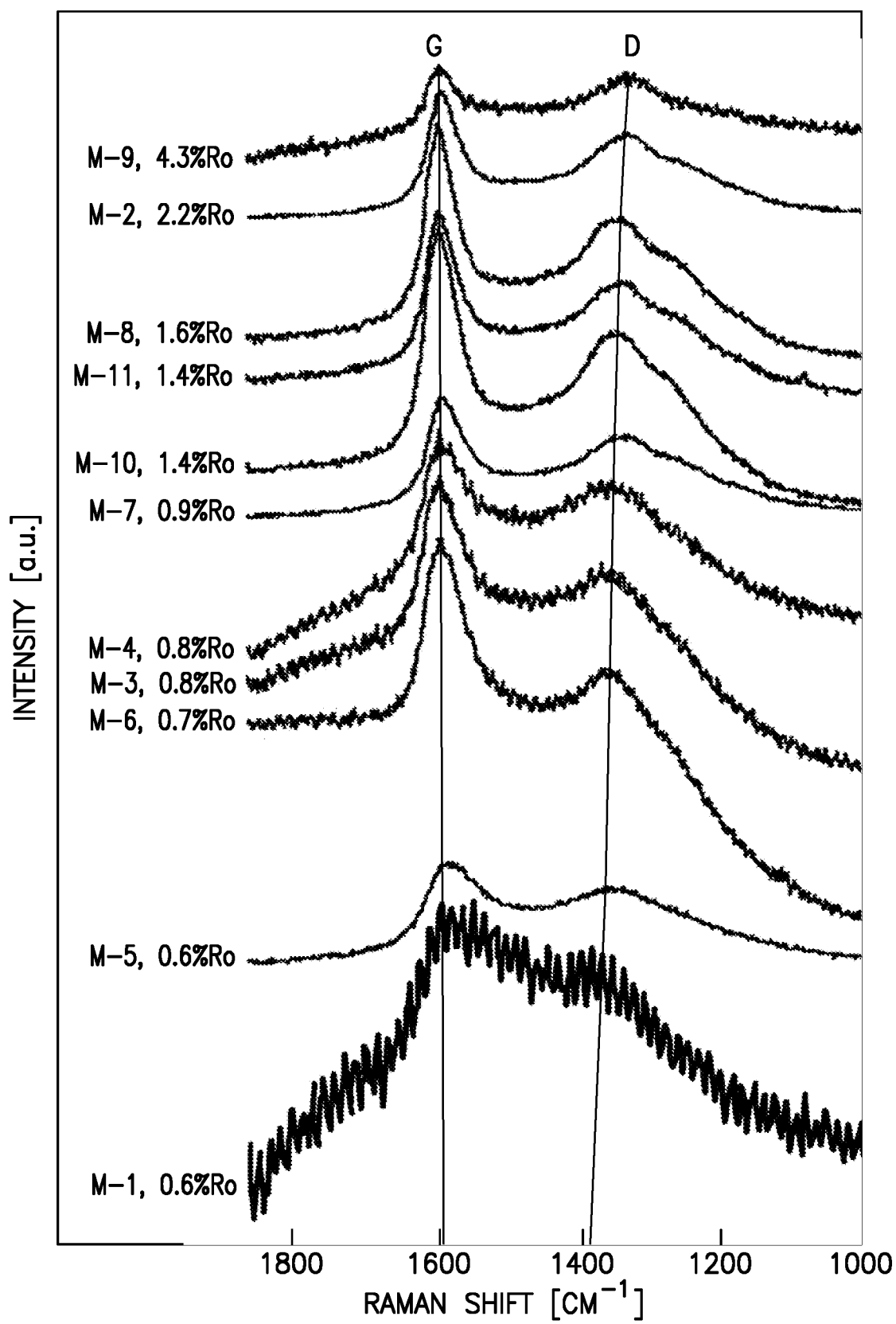

FIG. 3C shows measured Raman kerogen spectra for all mudstone samples that were studied stacked in order of their vitrinite reflectance (the most mature sample M-9 shown on top, and the least mature M-5 (and M-1) shown on the bottom. All but one sample (M-1) gave clean Raman spectra with clearly identifiable, characteristic G and D bands as is typical for kerogen. As may be seen from FIG. 3C where a line slightly angled from the vertical is used to show the trend in Raman shift D peak values, as the vitrinite reflectance increased, the Raman band separation (RBS) increased.

Figure 4:
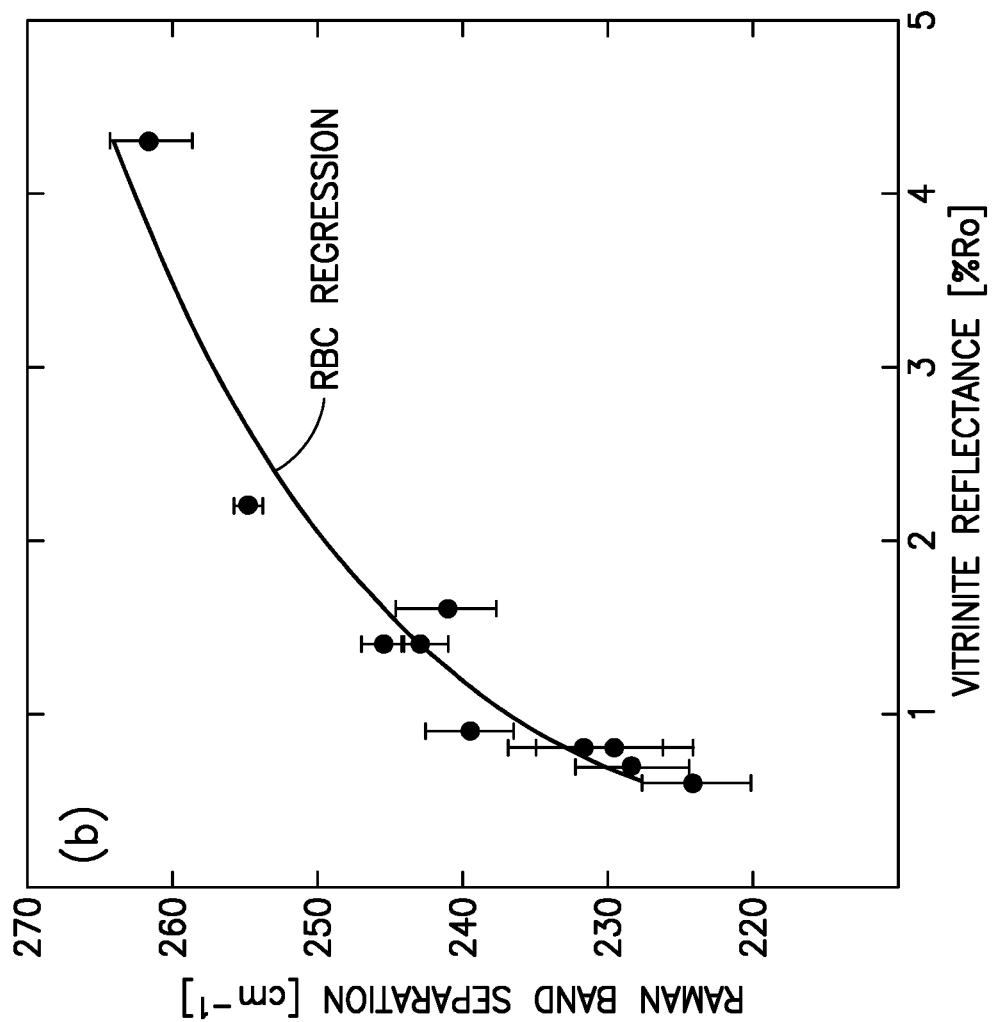
FIG. 4 is a plot showing a relationship between vitrinite reflectance and Raman band separation (RBS)

According to one aspect, based on the results shown in Table 1, and as shown in FIG. 4, the RBS may be plotted as a function of vitrinite reflectance, and a curve may be fitted to the plotted points, e.g., using a best-fit regression. The best-fit regression conducted on the results of Table 1 (omitting sample M-1 which was an outlier) and shown in FIG. 4 reveals that there is an excellent correlation between RBS calculated from the measured G and D1 band positions and the vitrinite reflectance.

value obtained from the Raman spectroscopic measurement on the cutting can be turned into a vitrinite reflectance equivalent value ($V_{Re}$) whether or not vitrinite is seen, present, or measurable in the cutting. That vitrinite reflectance equivalent value may be presented as representing the maturity of the respective formation interval from which the cutting was obtained. In addition, when cuttings from different depths in the formation are processed as previously described, the $V_{Re}$ values may then be plotted as a log.

Figure 5:
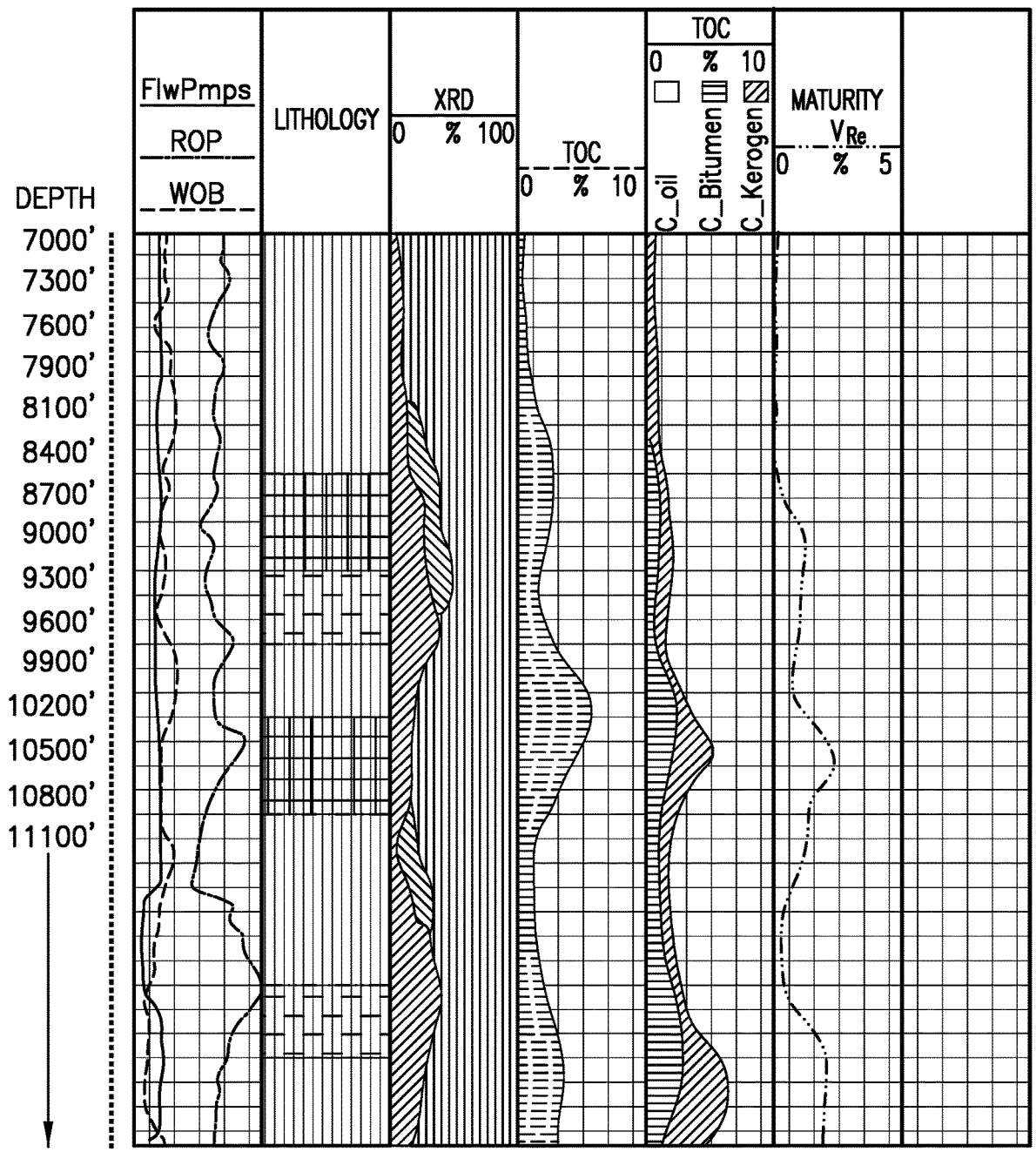
FIG. 5 is a hypothetical multi-log including a formation maturity log which plots a vitrinite reflectance equivalent $V_{Re}$ as a function of well depth.

A log which includes $V_{Re}$ values as a function of wellbore depth is seen in FIG. 5. For purposes herein the word "depth" when applied to the wellbore is to be understood broadly to include "distance". While determinations of $V_{Re}$ may be made based on cuttings obtained over particular depth (distance) intervals, and particular values may be shown at particular depths (distances) as is suggested by FIG. 5, smoothing filters may be also be used to generate a continuous log. The log may be included as one log of a multi-log printout as suggested by FIG. 5 which additionally includes, e.g., logs of rate of drill-bit penetration (ROP), weight on bit (WOB), total hydrocarbons (THC), total organic content (TOC), oil, bitumen and kerogen content, lithology, etc.

As previously indicated, in one embodiment, the peak fitting procedure used on the Raman spectrum may fit five peaks to the spectrum (as suggested by FIGS. 3A and 3B). In other embodiments, the peak fitting is conducted by fitting any number of peaks (e.g., two peaks, three peaks, four peaks, etc.) in order to derive G and D1 band positions of the Raman spectrum of kerogen with a lower standard deviation, and applying the procedure on multiple measurements of the same sample. In non-limiting examples, the peak shapes are modeled by a Voigt, Lorentzian or Gaussian function or a combination thereof.

As previously indicated, in one embodiment, a correlation between RBS and vitrinite reflectance was obtained by fitting a curve to particular data obtained from a variety of formation samples taken from different regions, ages, mineralogies and maturity levels. In other embodiments, other data and/or fitting techniques may be utilized. As a result, different equations may be generated and used to correlate RBS and the maturity prediction of an unknown sample.

In an embodiment, as previously indicated, the sample that is cleaned and subjected to a Raman spectrometer for analysis is a cutting obtained from a drilling operation. In alternative embodiments, the sample may be a chip or chunk from a reservoir core, plug or sidewall core.

In different embodiments, the kerogen being investigated in the samples is type I, type II, type III or type IV.

In different embodiments, the methods described herein are partly or completely automated. Thus, by way of example only, mud exiting a wellbore can be automatically forwarded through the sieve(s) 52, and material (e.g., cuttings) collected by the sieve(s) 52 can be automatically and periodically dumped onto or into the wash station 54. At particular time intervals, base oil, then water, then water and soap, and then pure water may be injected into the wash station, and after each injection, the cuttings and the injected liquid may be automatically agitated to conduct the washing. After the final pure water injection, the cleaned cuttings may be automatically forwarded (e.g., via a belt) to or through an oven 56 for drying, and then on to the observation station 58 which may include a UV lamp and a fluorescence detector under which the dried cleaned cuttings pass. If the fluorescence detector detects any signal, the cuttings may be automatically discarded or redirected to the wash station again for reprocessing. Otherwise, the cuttings may be automatically forwarded to the Raman spectrometer 60. While the cuttings will typically be investigated by the Raman spectrometer 60 under human control, it is possible to robotically place (and remove) the cuttings on the spectrometer stage and to automatically cause the laser to activate. Spectral acquisition and analysis (i.e., peak fitting and determination of G and D1 band positions and a resulting RBS) may be automatic, and the determination of the $V_{Re}$ as a function of the RBS may likewise be generated automatically by the processor 70. Finally, the $V_{Re}$ results may be automatically passed from the processor to a log plotter and a log may be generated on paper or on an electronic display medium.

While the methods described herein may be partly or completely automated, it will be appreciated that the converse is not true. In particular, the methods described cannot be carried out by a human without use of sophisticated equipment. For example, humans cannot conduct a Raman spectral analysis without a Raman spectrometer. In addition, it is not feasible for humans to reasonable conduct peak fitting of the spectral data efficiently without use of a processor.

In an embodiment, maturity windows (immature, oil, wet gas, dry gas) are assigned in the log manually and/or computed in an automated fashion. By way of example, where the formation maturity log shows a $V_{Re}$ of 0.5 or less, the formation maturity can be listed as "immature". For $V_{Re}$ values of between 0.5 and 1.0, the formation maturity can be listed as "oil". For $V_{Re}$ values of between 1.0 and 2.0, the formation maturity can be listed as "wet gas (condensate)". For $V_{Re}$ values above 2.0, the formation maturity can be listed as "dry gas".

According to one aspect, the methods described have an advantage in that they do not require the actual presence of vitrinite marcerals in a sample in order to provide an indication of the maturity of the sample. The method therefore allows maturity determination of pre-Devonian formations, which lack vitrinite and therefore do not allow maturity determination by standard vitrinite reflectance measurements.

Some of the methods and processes described above, can be performed by a processor. The term "processor" should not be construed to limit the embodiments disclosed herein to any particular device type or system. The processor may include a computer system. The computer system may also include a computer processor (e.g., a microprocessor, microcontroller, digital signal processor, or general-purpose computer) for executing any of the methods and processes described above.

The computer system may further include a memory such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device.

Some of the methods and processes described above, can be implemented as computer program logic for use with the computer processor. The computer program logic may be embodied in various forms, including a source code form or a computer executable form. Source code may include a series of computer program instructions in a variety of programming languages (e.g., an object code, an assembly language, or a high-level language such as C, C++, or JAVA). Such computer instructions can be stored in a non-transitory computer readable medium (e.g., memory) and executed by the computer processor. The computer instructions may be distributed in any form as a removable storage medium with accompanying printed or electronic documentation (e.g., shrink wrapped software), preloaded with a computer system (e.g., on system ROM or fixed disk), or distributed from a server or electronic bulletin board over a communication system (e.g., the Internet or World Wide Web).

Alternatively, or additionally, the processor may include discrete electronic components coupled to a printed circuit board, integrated circuitry (e.g., Application Specific Integrated Circuits (ASIC)), and/or programmable logic devices (e.g., a Field Programmable Gate Arrays (FPGA)). Any of the methods and processes described above can be implemented using such logic devices.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims. Moreover, embodiments described herein may be practiced in the absence of any element that is not specifically disclosed herein.

In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

The invention claimed is:

1. A method for determining the maturity of a formation sample, comprising:
   cleaning the formation sample to remove residues of drilling fluid and reservoir fluid to obtain a cleaned sample;
   performing Raman spectroscopic measurements on the cleaned sample to obtain a Raman spectrum for the sample;
   fitting at least a G (graphite) peak and a D1 (defect) peak to the Raman spectrum to obtain Raman shift values for the G peak and the D1 peak and a Raman band separation (RBS) value;
   using the RBS to generate a vitrinite reflectance equivalent ($V_{Re}$) value using a relationship correlating RBS to $V_{Re}$; and
   displaying the $V_{Re}$ as an indicator of formation sample maturity for a depth in the formation from which the sample was obtained.

2. The method of claim 1, wherein said relationship is RBS=c1 ln($V_{Re}$)+c2, where c1 and c2 are constants.

3. The method of claim 1, wherein the fitting of at least a G peak and a D1 peak comprises fitting said G peak, said D1 peak and three additional peaks.

4. The method of claim 3, wherein said fitting comprises using peak shapes modeled using a Voigt, Lorentzian or Gaussian function or combination thereof.

5. The method of claim 1, wherein the formation sample is selected from a group consisting of: cores, chunks, chips and cuttings from the formation.

6. The method of claim 1, wherein said performing Raman spectroscopic measurements comprises utilizing a Raman laser having a wavelength of approximately 532 nm.

7. The method of claim 6, wherein said performing Raman spectroscopic measurements comprises analyzing signals occurring in the Raman spectroscopic measurements between 200 $cm^{-1}$ and 1877 $cm^{-1}$.

8. The method of claim 1, further comprising, after said cleaning and before said performing Raman spectroscopy, subjecting the cleaned sample to ultraviolet light and looking for a resulting fluorescence signal, and subjecting the cleaned sample to additional cleaning if a fluorescence signal is seen.

9. The method of claim 8, wherein said additional cleaning comprises washing the sample with a base oil, then water, then water and soap, and then pure water.

10. The method of claim 1, wherein said cleaning comprises washing the sample with a base oil, then water, then water and soap, and then pure water.

11. A method for determining the maturity of a formation sample, comprising:
   obtaining cuttings of the formation sample from drilling fluid at a wellbore;
   at the wellbore, cleaning the cuttings to remove residues of drilling fluid and reservoir fluid to obtain a cleaned sample;
   at the wellbore, performing Raman spectroscopic measurements on the cleaned sample to obtain a Raman spectrum for the sample;
   fitting at least a G (graphite) peak and a D1 (defect) peak to the Raman spectrum to obtain Raman shift values for the G peak and the D1 peak and a Raman band separation (RBS) value;
   using the RBS to generate a vitrinite reflectance equivalent ($V_{Re}$) value using a relationship correlating RBS to $V_{Re}$; and
   displaying the $V_{Re}$ as an indicator of formation sample maturity for a depth in the formation from which the sample was obtained.

12. The method of claim 11, further comprising, at the wellbore, after cleaning and before performing Raman spectroscopic measurements, drying the cleaned sample and subjecting the cleaned sample to ultraviolet light and looking for a resulting fluorescence signal, and subjecting the cleaned sample to additional cleaning if a fluorescence signal is seen.

13. The method of claim 12, wherein said additional cleaning comprises washing the sample with a base oil, then water, then water and soap, and then pure water.

14. The method of claim 12, wherein said relationship is RBS=c1 ln($V_{Re}$)+c2, where c1 and c2 are constants.

15. The method of claim 14, wherein the fitting of at least a G peak and a D1 peak comprises fitting said G peak, said D1 peak and three additional peaks, and said fitting comprises using peak shapes modeled using a Voigt, Lorentzian or Gaussian function or combinations thereof.

16. The method of claim 15, wherein said performing Raman spectroscopic measurements comprises utilizing a Raman laser having a wavelength of approximately 532 nm, and analyzing signals occurring in the Raman spectroscopic measurements between 200 $cm^{-1}$ and 1877 $cm^{-1}$.

17. A method for providing indications of the maturity of a formation traversed by a wellbore as a function of formation depth, comprising:
   at the wellbore, obtaining separate cutting samples of the formation from wellbore drilling fluid respectively representing the formation at multiple formation depths;
   at the wellbore, cleaning the cutting samples to remove residues of drilling fluid and reservoir fluid to obtain cleaned samples respectively representing the multiple formation depths;
   at the wellbore, for each of the cleaned samples, performing Raman spectroscopic measurements to obtain Raman spectra for the samples respectively representing the multiple formation depths;
   for each formation depth, fitting at least a G (graphite) peak and a D1 (defect) peak to each Raman spectrum to obtain Raman shift values for the G peak and the D1 peak and a Raman band separation (RBS) value for that formation depth;
   for each formation depth, using the RBS to generate a vitrinite reflectance equivalent ($V_{Re}$) value for that formation depth using a relationship correlating RBS to $V_{Re}$; and
   for each formation depth, displaying in log format the $V_{Re}$ as an indicator of formation sample maturity for that depth in the formation.

18. The method of claim 17, wherein said relationship is $RBS = c1\ \ln(V_{Re}) + c2$, where c1 and c2 are constants.

19. The method of claim 17, wherein the fitting at least a G peak and a D1 peak comprises fitting said G peak, said D1 peak and three additional peaks, and said fitting comprises using peak shapes modeled using a Voigt, Lorentzian or Gaussian function or a combination thereof.

20. The method of claim 17, wherein said performing Raman spectroscopic measurements comprises utilizing a Raman laser having a wavelength of approximately 532 nm, and analyzing signals occurring in the Raman spectroscopic measurements between 200 $cm^{-1}$ and 1877 $cm^{-1}$.

* * * * *